United States Patent

Tofighi et al.

[11] Patent Number: 5,980,482
[45] Date of Patent: *Nov. 9, 1999

[54] MIXING DEVICE

[75] Inventors: Aliassghar Tofighi, Belmont, Mass.;
Alfred V. Vasconcellos, Cranston, R.I.;
Katherine Jacobs, Sagamore Beach;
Pramod Chakravarthy, Cambridge,
both of Mass.

[73] Assignee: Etex Corporation, Cambridge, Mass.

[ * ] Notice: This patent is subject to a terminal disclaimer.

[21] Appl. No.: 08/948,435

[22] Filed: Oct. 10, 1997

Related U.S. Application Data

[63] Continuation-in-part of application No. 08/728,440, Oct. 10, 1996.
[51] Int. Cl.$^6$ .................................................. A61M 37/00
[52] U.S. Cl. ............................... 604/82; 604/37; 604/212
[58] Field of Search ............................... 604/212, 58, 59, 604/57, 82, 83, 84, 85, 86, 88, 89, 37, 142, 257; 222/92, 94, 95, 420

[56] References Cited

U.S. PATENT DOCUMENTS

| | | |
|---|---|---|
| 1,004,103 | 9/1911 | Tacey . |
| 2,112,581 | 3/1938 | Tacey . |
| 4,950,237 | 8/1990 | Henault et al. . |
| 5,453,645 | 9/1995 | Faccioli et al. . |

FOREIGN PATENT DOCUMENTS 2838222  3/1980  Germany .

OTHER PUBLICATIONS

Thomas Register 1994, Adhesives, p. 254.

*Primary Examiner*—Corrine McDermott
*Assistant Examiner*—Kent Gring
*Attorney, Agent, or Firm*—Clark & Elbing LLP

[57] ABSTRACT

A mixer for the mixing of components, comprising a continuous inner surface that is non-retaining to the components, wherein a first portion of the inner surface opposably contacts a second portion of the inner surface during mixing, and a means for supplying a component to the mixer; a kit including the mixer, and methods of using the mixer to prepare compositions.

23 Claims, 6 Drawing Sheets

5,980,482

MIXING DEVICE

RELATED APPLICATION

This application is a continuation-in-part application of U.S. Ser. No. 08/728,440 filed on Oct. 10, 1996, hereby incorporated by reference in its entirety.

BACKGROUND OF THE INVENTION

The field of the invention is containers for shipping, storing, and activating biologically active powders. One such powder is bioceramic precursor powder which is mixed with a liquid to form a paste which is inserted where needed to make synthetic bone.

SUMMARY OF THE INVENTION

The invention features a mixing area or portion having a continuous inner surface that is non-retaining to the components to be mixed, wherein a first portion of the inner surface opposably contacts a second portion of the inner surface during mixing. For example, the mixing area or portion can be a flexible mixing pouch which has a continuous inner surface that is non-retaining to the components, wherein a portion of the inner surface opposably contacts another portion during the mixing of two or more components. The disclosed mixer devices include the mixing area or portion (e.g., the device can include a mixing pouch wherein a portion of the pouch has a continuous inner surface that is nonretaining) and a means for supplying one or more additional components to the mixing pouch for mixing with a first component. In use, the mixing pouch generally includes a pre-measured amount of the first component. For example, the first component can be contained within the pouch and be a medically useful substance or mixture, and a second component can be a liquid. The first component can include a powder, such as a bioceramic precursor powder.

In one embodiment, the means for supplying the second component to the pouch includes a neck attached to the pouch. The neck can be removably or permanently attached to the pouch. The supplying means can further include additional features such as a cap, plug, or cover for the neck; a needle port or needle penetrable material on the pouch or on the neck; a needle or tube attached to the pouch, the neck, or a valve opening; a manual valve or a check valve attached to the pouch or the neck; a protecting member and a handling means, including a holder or cartridge; a permeable membrane; a frangible membrane attached to the inner surface of the neck or the pouch; or a combination thereof. A valve can be a one-way valve or a multiple-way valve. One embodiment includes a retaining structure attached to the inner surface of the neck. Thus, after the frangible membrane is broken, the retaining structure separates pieces of the broken frangible membrane from the components to be mixed. The mixer can be adapted to be used with a mechanical mixing device, or to be manually mixed.

After mixing, the mixed contents of the pouch is removed. In one embodiment, the pouch can be opened with a cutting instrument, such as a knife or scissors. Alternatively, the mixer device can be adapted to include a means for evacuating or expelling the mixed components, such as a bioceramic paste, from the mixing pouch. Such expelling means include a valve attached to the neck through which mixed components can be ejected. The valve through which mixed components are ejected can also be a means for supplying a second component. The same or different valve openings can be used to introduce and expel material. The expelling means can include a needle or a tube attached to the pouch, the neck, or a valve. Mixed components can thereby be ejected through the needle or tube.

A preferred embodiment includes a single neck attached to the mixing pouch. The neck is configured for introducing a second component into the mixing pouch and for expelling mixed components from the pouch. The mixing pouch is preferably formed of an elastic material and can be sterilized.

The invention also features a method for preparing a medically useful composition, such as a bioceramic paste, using the disclosed mixer. The method includes a) providing a disclosed mixer wherein the first and second components are in sterile form; b) introducing the second component, e.g., a liquid, through the supplying means; c) mixing the combined components in the mixing pouch; and d) removing the components from the pouch. The disclosed mixer can be, for example, a mixer including a first component which is medically useful and a second component which is a liquid.

Another embodiment of the invention is a kit that includes: a) a disclosed mixer wherein the first component is in sterile form; and b) a syringe containing the second component in sterile form. The first and second components are preferably premeasured. A third or a third and fourth component may be included.

The invention facilitates the complete mixing of a powder and a liquid. The single piece construction of the device means that there are no seams or corners in the pouch where unmixed material might otherwise be trapped. Another advantage of the mixer of the invention is that it is inexpensive to produce, which is especially advantageous in light of the fact that it is intended to be disposable.

Other features and advantages of the invention will be apparent from the following description of the preferred embodiments thereof, and from the claims.

BRIEF DESCRIPTION OF THE DRAWINGS

FIG. 6B includes a cap or plug on the end of a needle, and a needle penetrable material on the neck. FIG. 6C includes a valve attached to the neck and a curved needle. FIG. 6D includes a needle at an angle to the neck and a needle port.

FIG. 7A has one frangible membrane attached to the neck. FIG. 7B has two frangible membranes attached to the neck. FIG. 7C has a frangible membrane and a retaining structure. FIG. 7D has a frangible membrane attached to the pouch.

DETAILED DESCRIPTION

The invention relates to a mixing device having a mixing area or mixing portion with a continuous inner surface that is non-retaining with respect to the components to be mixed. The mixing portion also has opposable sides that intermittently or temporarily contact each other during manual or mechanical mixing. A mixing area is the portion of the mixing device which comes into contact with the combined materials to be mixed. In one preferred embodiment, the mixing device comprises a pouch, wherein the pouch includes a mixing area having a continuous inner surface that is non-retaining with respect to the components to be mixed.

In the mixing process, two functions must occur: the movement of the pouch material in opposition to itself should be easily performed, in most cases by hand, and there must be no structures or features within or on the inner surface of the pouch which would tend to trap one or more of the components to be mixed or otherwise deleteriously affect the mixing process and result in incomplete mixing. Since the pouch is flexible, these same considerations apply to the outer topography of the pouch, as they can affect the shape of the pouch inner surface during the mixing process. Pouch designs meeting the above criteria are said to have a mixing area with a non-retaining inner surface. The features of the inner pouch surface should not significantly hinder the evacuation of the mixed components or reaction products therefrom.

The requirements regarding the surface topography and geometry to produce a non-retaining surface can vary, depending on the type of components to be mixed. For example, in the case of dry powders, preferred pouches will be smooth and free of entrapping edges, pits, corners, or seams. In other embodiments, one or more of these potentially entrapping features may be present, provided their dimensions are significantly smaller than the grain or particulate size of the powder. Thus mixing of powders with a minimum particle size of 100 $\mu$m diameter would not be adversely affected by the presence of 1 $\mu$m diameter pits or 1 $\mu$m high edges. In the case of the mixing of low viscosity liquids or gases, edges may be tolerated provided they are not so severe as to hinder pouch movement during mixing or hinder the evacuation process.

Structure

Figure 1:
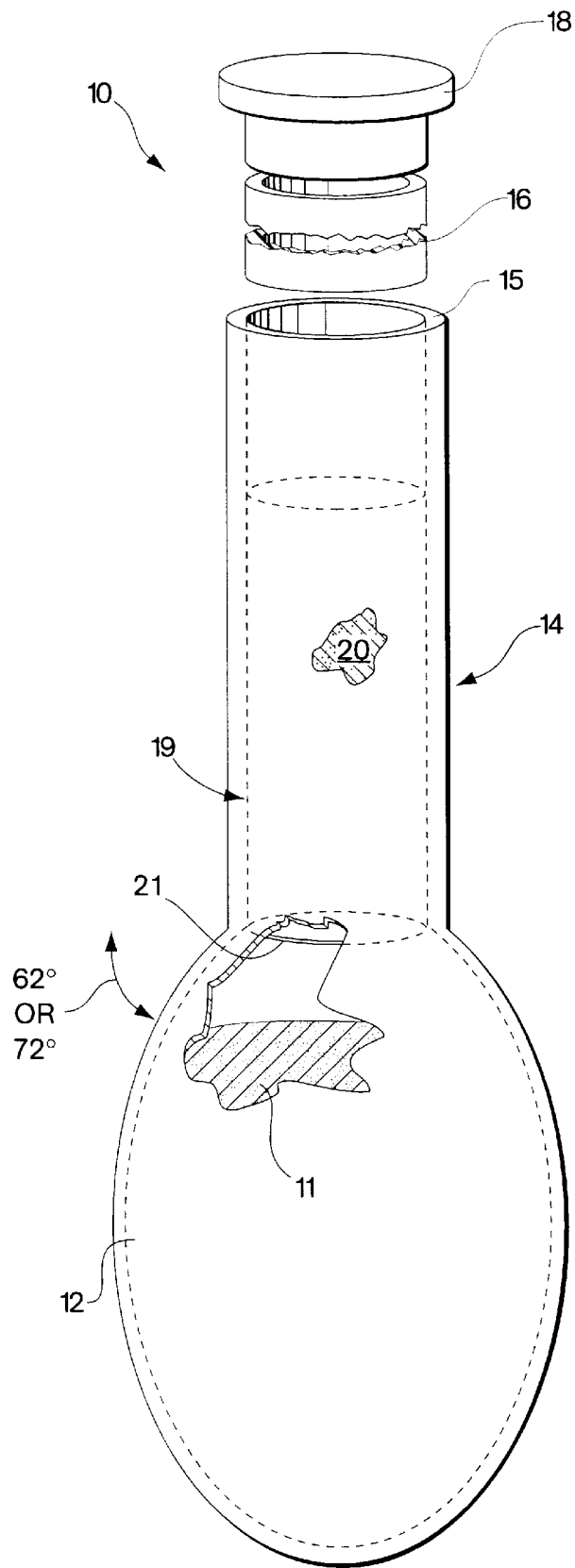
FIG. 1 is a plan view of a mixer of the invention.
Figure 2:
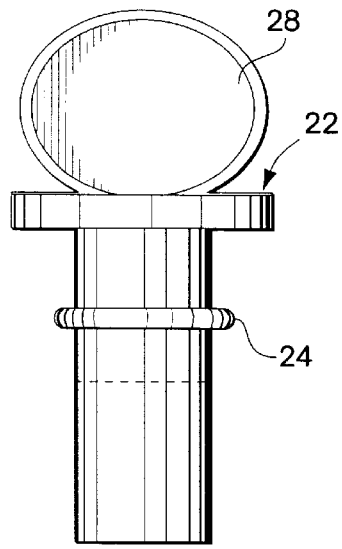
FIGS. 2, 3, and 4 are, respectively, front, side, and perspective views of a stopper for the neck of the mixer, showing the protecting member.
Figure 3:
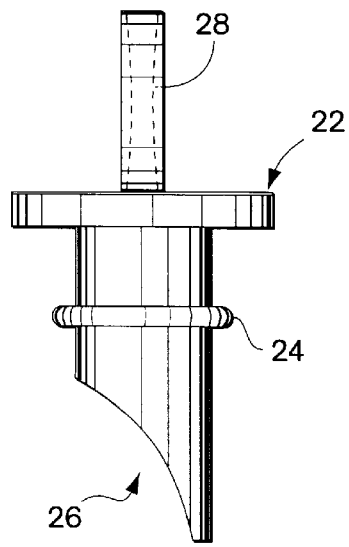
Figure 4:
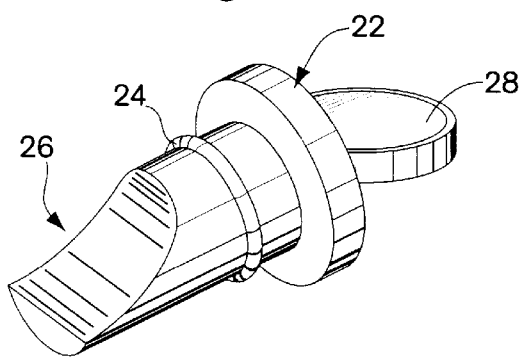
Figure 5:
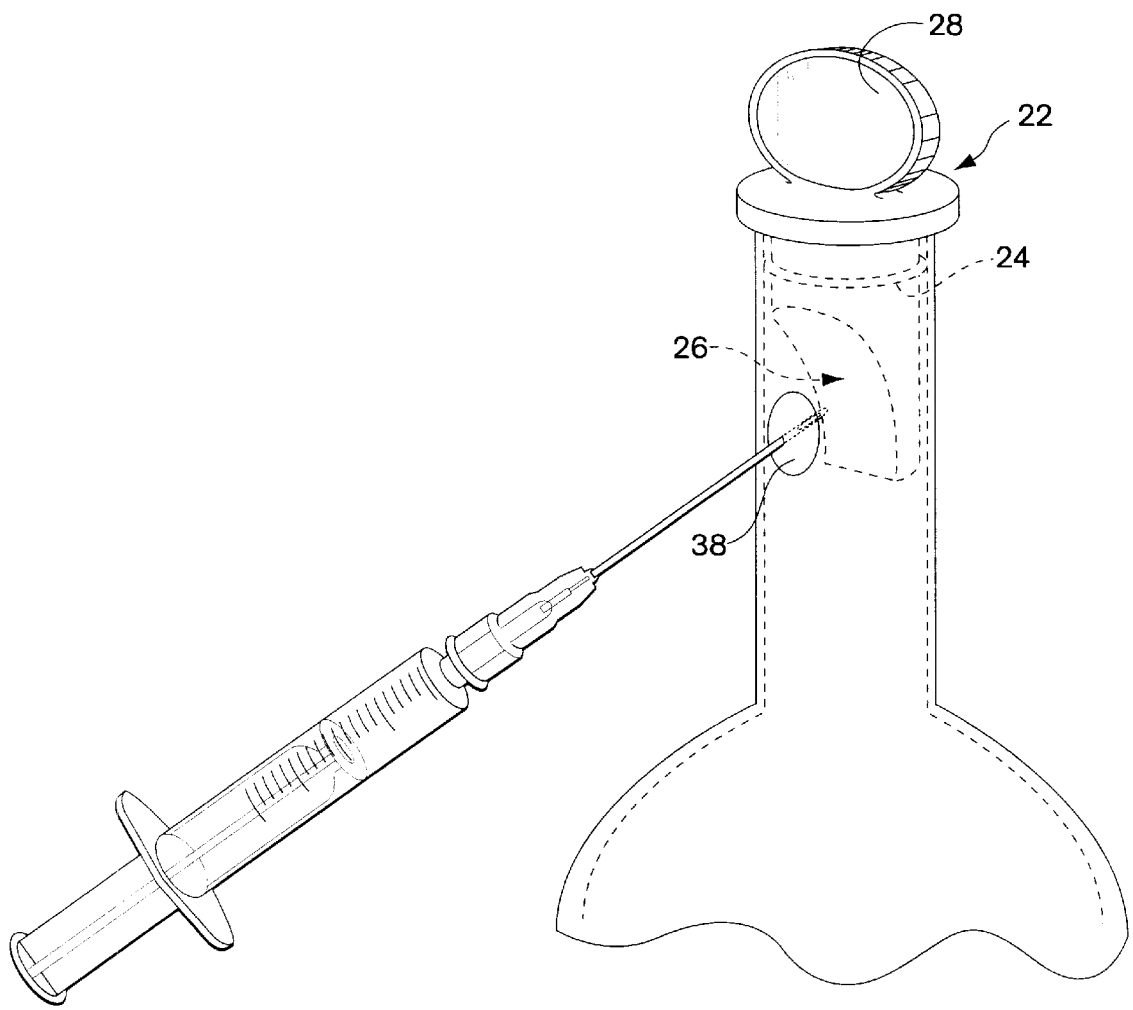
FIG. 5 is a side view of the pouch of the invention, with a syringe, showing the inside protecting member.

FIG. 1 illustrates a preferred embodiment of a mixer 10. Bioceramic precursor powder 11 is held inside a pouch 12 which is formed of one piece of flexible elastic material, which might be, for example, polyurethane, silicone, Krayton, polyethylene, rubber latex, or another elastomer. Neck 14, with mouth 15, is formed of the same piece of material as pouch 12. Pouch 12 and neck 14 are formed so as to have no seams which might hinder the uniform mixing of powder 11. A protective insert 16 made, for example, of polypropylene tubing, may be used to reinforce neck 14. A stopper 18, preferably made of rubber, closes the mouth 15. The dimensions of mixer 10 are: height of pouch 11: 4.5 cm; height of neck 14: 4.5 cm; width of pouch: 0.3 cm; volume of pouch, not including neck: 15 ml. Alternative measurements are: height of pouch: 3.4 cm; height of neck: 3.4 cm; width of pouch: 1.3 cm; volume of pouch: 5 ml.

Manufacture

There are several ways to manufacture mixer 10 using known container manufacturing techniques. For example, the mixer can be injection molded, dipping molded, rotational molded, or blow molded. All of these methods are conventional and well-known and need not be described herein.

The pouch 12 should be made of a flexible material. The pouch has opposable sides which contact each other when the pouch is manually or mechanically compressed during mixing. In some instances, the pouch should be flexible enough to be compressed by hand. In other embodiments, where mixing is carried out by a mechanical or other non-manual approach, a more rigid (although still somewhat flexible) material may be employed. In some embodiments, the entire inner surface of the device is non-retaining.

The neck 14 may be manufactured to be continuous with pouch 12, or may be affixed separately. The neck may be of any useful length and does not generally participate in the mixing function, but rather provides a means for the storage of additional components, means for introducing components to be mixed, means for expelling the mixed components, and space to add additional features such as caps, labels, handles, injection ports, vents, attachments and the like.

Any form of attachment between the neck and the pouch may be used as long as it does not tend to trap components to be mixed or adversely interfere with the entry or evacuation of components into or out of the mixing area of pouch 12. The requirements for materials used in manufacturing the neck, or the means of attaching the neck to the pouch will be dictated by the intended functionality of the neck. The neck may be manufactured continuously with the pouch as a single entity, or may be attached to the pouch by any suitable means such as but not limited to a connector attached to the pouch by glue, compression fitting, friction fitting, or threads. The connector may be a distinct piece or continuous with either the pouch or the neck.

Additional features attached to the neck or the pouch include protective inserts, caps, ports, check valves, manual valves, vents, plugs, needles, cartridges, handles, labels, and holders. Manufacture and attachment of such additional features will be guided by considerations known in the art. The sealed mixer may be sterilized if required.

In the general construction of the mixer, multiple bulbs may be joined at the neck to allow discrete mixing steps. Mixtures in different bulbs can then later be combined. The mixer can be used to mix not just bone paste, but a variety of materials. The mixer is not limited to holding a powder, but can be used to mix liquids, pastes, powders, or combinations. The mixer may also include venting means for gases produced by chemical reactions of mixed components.

Use

The disclosed mixer allows for the storage, shipping, combining and mixing of components without the need for opening the package prior to mixing. Thus the invention is particularly well suited for the shipment of sterile powders for sterile reconstitution with liquids or sterile mixing with other powders without the risk of contamination. In one embodiment, a mixer of the invention is used as a package for shipping, storing, and mixing a bioceramic precursor powder for use as a surgical synthetic bone replacement material which is stored in powder form and mixed with a liquid immediately before use to form a paste. Many bioceramic precursor powders are known, e.g., those disclosed in U.S. Pat. No. 5,178,845, hereby incorporated by reference.

The mixer is shipped from a manufacturer to a medical center in the form of a kit which includes a sterile pre-filled syringe and needle containing sterile water or buffer. The mixer is sealed and sterile, and contains the bioceramic precursor powder. The kit also optionally includes a spatula and/or syringe for the application of the paste by the user, and an optional portable mechanical mixer. The mixer and powder are stored in a medical facility until needed. When there is a surgical procedure where synthetic bone is needed, liquid is injected into the pouch through the neck above the end of the protective member present on the stopper and the powder-liquid mixture is mixed by hand while still inside the pouch. When the components are mixed sufficiently to form a paste, the neck is cut, and the paste is squeezed out of the pouch into a syringe or a petri dish, depending on the surgical requirements. The mixer is discarded after extrusion of the paste.

Figure 7A:
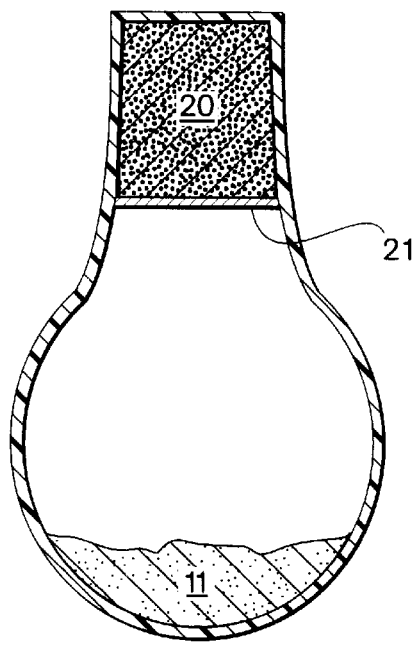
FIGS. 7A–7D are cross-sectional views of embodiments having frangible membranes attached to the inner surface of the neck of the pouch.
Figure 7B:
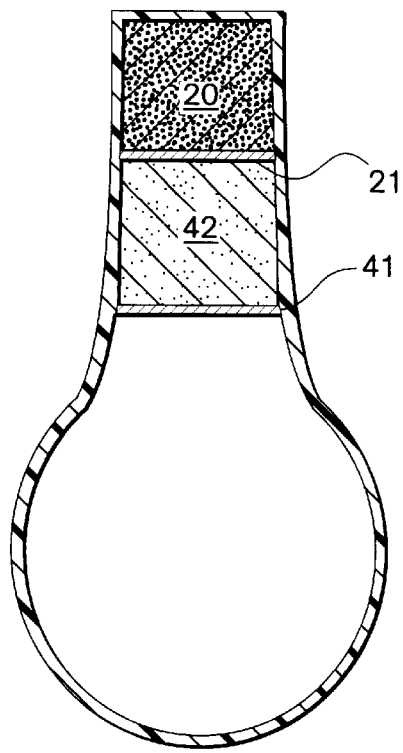
Figure 7C:
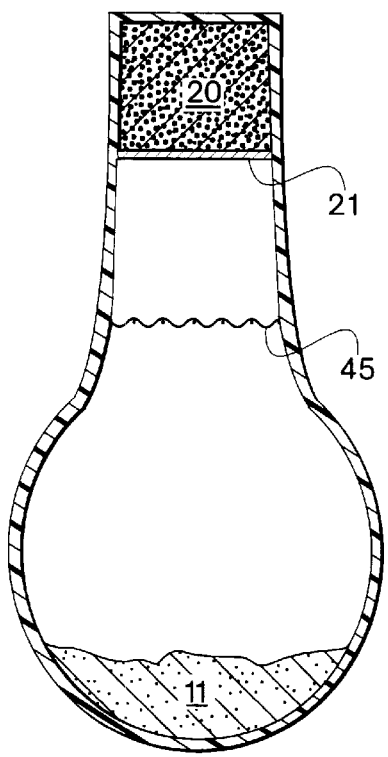
Figure 7D:
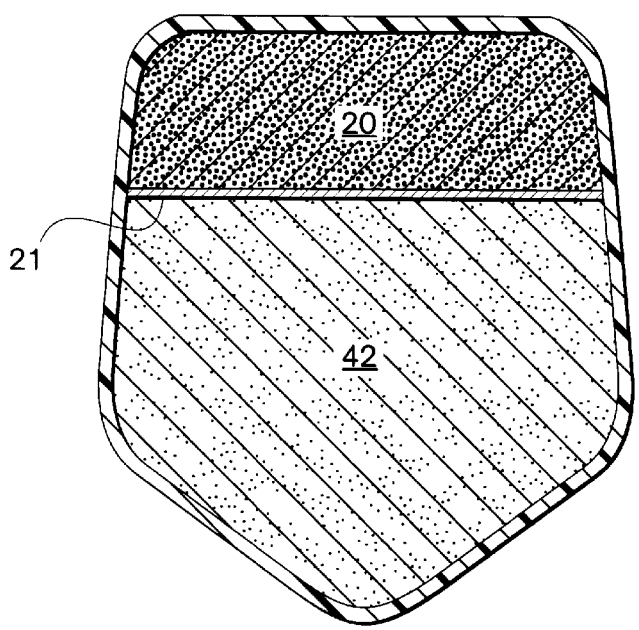

Referring to FIG. 1, in mixer 10, the neck includes a reservoir 19 containing a component 20 to be mixed with a second component 11 within the pouch. The frangible seal 21 between the storage compartment and the pouch insures separation of the components during shipping and storage. Component 20 is introduced into the pouch by breaking the frangible seal 21, and transferring component 20 into the pouch, where mixing is carried out (see also FIGS. 7A–7D). Similarly, component 42 is introduced by breaking frangible membrane 41 (FIGS. 7B and 7D). Frangible membranes 21 and 42 can be broken simultaneously or in series to accommodate a variety of mixing sequences.

Referring now to FIGS. 2, 3, 4, and 5, a preferred stopper for insertion into the neck of the mixer is shown, including head 22, lip 24, and injection site 26 and handling means 28. Water is added to the mixer by insertion of a needle into the upper neck region; the protective member protects the user from accidentally inserting the needle entirely through the device and causing injury to himself.

In preferred embodiments, the pouch has a capacity of about 1 to 20 ml, and allows convenient manual mixing of components contained therein. In smaller sizes (less than 10 ml) mixing is accomplished by manually kneading, pinching, or squeezing the flexible pouch, for example, with the thumb and forefinger of one hand. In larger sizes, the fingers of both hands may be employed simultaneously, or other methods such as use of a fist or palm of the hand may also be effective. Larger embodiments are mixed by mechanical means, for example, including a holder and one or more plungers. In one embodiment, reproducible and highly controlled mixing of the components within the mixer is obtained through the use of a mechanical mixer adapted to accept the flexible pouch and to mix the components therein.

Any number of components may be introduced into the pouch provided their total volume does not exceed the volume of the pouch itself. Likewise, any introducer means appropriate for supplying the material to be mixed to the pouch may be employed. While it is possible for introducer means to exist on the pouch itself (e.g., a syringe needle penetrable pouch material, or the use of a gas or liquid permeable or semi-permeable pouch), in most cases this will be avoided because the presence of the introducer means can deleteriously affect the non-retaining character of the pouch inner surface. The means for introducing additional components to the pouch will most often be present in the neck or specific attachments thereto. Suitable introducer means include but are not limited to mechanical valves, check valves, ports, permeable or semi-permeable membranes, needle septa, needles, frangible membranes, semi-permeable membranes, and the like.

The neck generally performs two functions, supplying the second component, e.g., a liquid, to the pouch and ejecting the mixed components from the pouch. The neck may include several compartments which can be breached to introduce their contents into the pouch. The neck can also be reinforced with a protective insert, and/or fitted with a handle to facilitate holding the mixer.

In the preferred embodiment, a liquid second component is supplied to the pouch with a syringe through a rubber stopper. Where a substance is introduced via a syringe needle through the upper portion of the neck, a specialized stopper is used. The stopper limits the possibility of an accidental needle stick to the user by preventing unintended passage of the needle entirely through the neck. The specialized stopper, shown in FIG. 5, features a protecting member, generally flat, which extends into the neck. The needle is introduced into the neck at a point above the lower extent of the protecting member. In embodiments wherein a syringe is used for the introduction of a component, the mixed contents can be expelled back into the same syringe or expelled into a different syringe.

In another embodiment, a component is introduced into the pouch, or mixed components are removed from the pouch, via a peacock or manual valve (one-way or multiple-way valve) attached to the neck of the mixing device. Multiple valves include two-way valves, three-way valves, four-way valves, five-way valves, and so on. One or more components can be simultaneously or sequentially introduced into the mixing pouch through a multiple valve when opened in one direction without material flowing back out. The mixed contents of the mixing pouch can also be removed or extruded through the valve when opened in the opposite direction. The multiple valve also has a closed position that provides a closed, optionally sterile system during mixing. Examples of check valves include the 500 Series check valves available from Smart Products, San Jose, Calif., although there are other suitable valves that are small, corrosion resistant, chemically inert to the components to be mixed, and have a cracking pressure between about 0.5 and 10.0 psi. The cracking pressure may vary depending on the inner diameter of the valve openings, a needle or tube, and the viscosity or particle size of the mixed components.

As an alternative to a manual valve, an embodiment can include a check valve that relies on the crack pressure concept. A check valve may be a one-way check valve or a multiple-way check valve (e.g., two-way, three-way, or four-way check valve). The cracking pressures of a check valve is the pressure at which the valve allows material to flow. For example, for a liquid to push into the device, the required pressure may be about 3 psi. Pressure greater than or equal to the crack pressure is necessary to initiate and sustain flow through a valve into the mixing during the passage of the component or mixture. A valve may be made of a hard plastic material, or another material such as hard rubber, a metal, or a metal alloy. In some cases, the valve is used in combination with a selectively permeable membrane that allows differential flow of components, e.g., allow liquids to pass through but retain powders or particles.

Figure 6A:
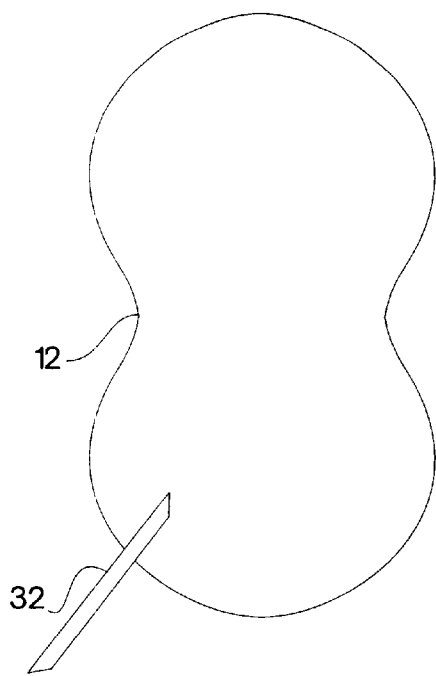
FIGS. 6A–6D are side views of embodiments having a needle or tube 32 attached to the pouch or the neck of the mixing device to allow mixed contents to be expelled.
Figure 6B:
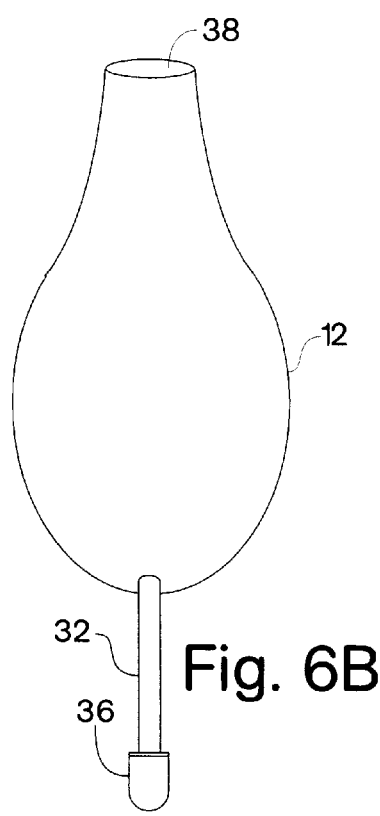
Figure 6C:
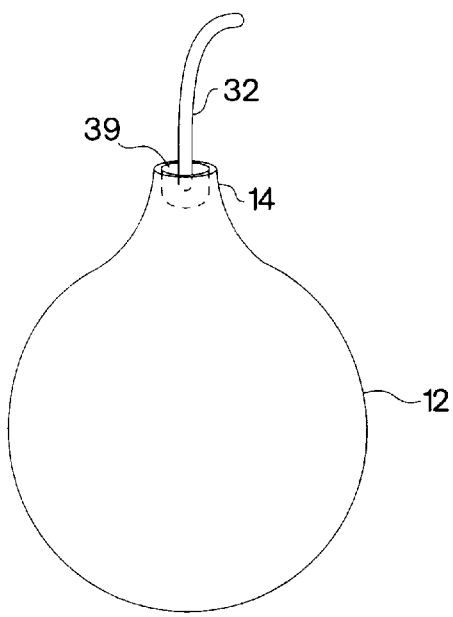
Figure 6D:
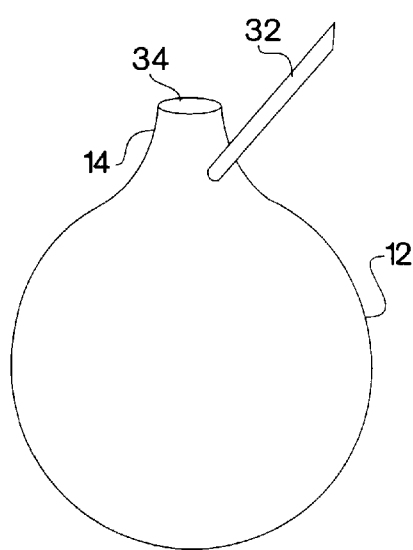
Figure 8A:
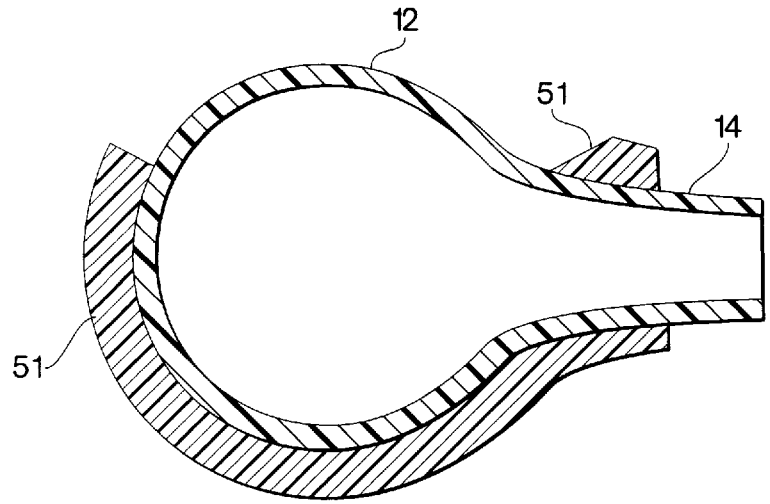
FIGS. 8A and 8B are cross-sectional views, respectively, of embodiments having a holder or handling means, and a cartridge and a plunger.
Figure 8B:
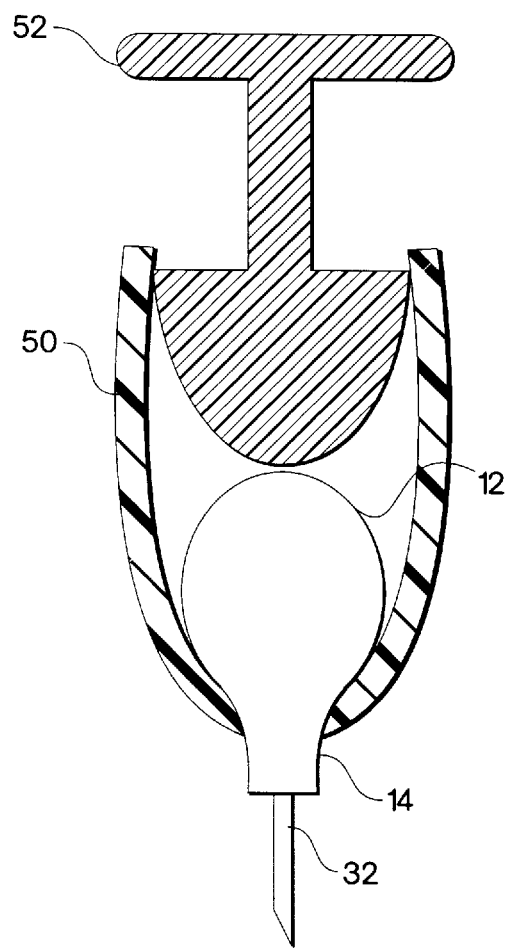

Yet another embodiment features a needle or tube 32 or 34 attached to pouch 12 or neck 14 of the mixing device to allow the contents of the mixing pouch to be expelled from the pouch through the needle, e.g., by manually or mechanically squeezing the pouch (FIGS. 6A–6D). The needle or a tube, with a removable seal or screwable or snap-off cap 36, may be glued to the pouch, for example, at an angle to the neck or opposing the neck (FIG. 6B). The needle or tube may be straight, angled, or curved (FIG. 6C), and may be attached at an angle (FIG. 6D) or perpendicular to the tangent of the pouch (FIG. 8B). The shape of the needle or tube, and the angle at which it is attached relative to the pouch or neck, is chosen for convenience in mixing and expelling the mixed contents. FIG. 6B includes a cap or plug 36 on the end of needle 32 and a needle penetrable material 38 on the neck. FIG. 6C includes a valve 39 attached to the neck and a curved needle 32. FIG. 6D includes a needle 32 at an angle to the neck and a needle port 34. Suitable needles include those having a gauge of 16 or greater, such as 18 or 24 or higher.

In another embodiment, the mixing device includes a membrane, preferably a frangible membrane. A frangible membrane 21, 23, or 41 (FIGS. 1 and 7A–7D) is a thin, generally plastic, material that is impermeable and inert to the contents of the mixing pouch, and yet easily broken by physical force or pressure. The membrane 21 provides one or more barriers to separate two or more pre-measured components prior to mixing, e.g., during packaging, shipping, and storage (FIGS. 7B and 7D). A membrane can be within the neck of the pouch (FIGS. 7A–7C), or within the pouch itself (FIG. 7D). After the membrane is broken, multiple components (e.g., components 20 and 42 in FIGS. 7B and 7D) come into contact with each other and/or an additional component added by a supplying means. An embodiment may contain one or more frangible membranes (FIGS. 7A–7D). The membrane does not shred or disintegrate into pieces which could mix with the contents of the pouch. Alternatively, there is a retaining structure 45, such as a filter, mesh, or screen that catches pieces of the membrane, thereby preventing the pieces from mixing with the components in the pouch (FIG. 7C). In addition to plastics such as polyethylene, polyvinyl chloride, polycarbonate, and polyethylene glycol, the membrane may comprise materials such as non-woven papers, ceramics, or glass.

Following completion of the mixing process the mixed components (or reaction products or combination thereof) may be stored within the pouch. The mixed components can be ejected in a variety of ways. The mixed contents can be removed providing an opening, for example, by removing a cap or a plug or by cutting the neck or the pouch. The contents are removed with an implement such as a syringe, a pipette or a spatula. Alternatively, the neck may be fitted with a valve or needle through which the mixture is squeezed out. The flexible nature of the pouch facilitates extrusion of the components, since a pouch may be squeezed or rolled like a toothpaste tube. Manual squeezing includes squeezing or rolling the mixed contents out of the pouch. Mechanical squeezing also includes the optional use of a cartridge 50 or a holding or handling device 51, either of which may be fitted with a plunger or pestle 52 to provide added control or leverage during mixing or evacuation of the pouch after mixing (FIGS. 8A and 8B). In some embodiments, a needle is attached to the cartridge or holding device, or to the neck of the pouch. The plunger is pushed, thereby expelling the contents of the pouch through a valve or a needle. In the preferred embodiment, a neck is cut with scissors, and the surgeon squeezes the mixture out of the pouch.

OTHER EMBODIMENTS

From the above description, one skilled in the art can easily ascertain the essential characteristics of the present invention, and without departing from the spirit and scope thereof, can make various changes and modifications of the invention to adapt it to various conditions. Thus, other embodiments are within the claims.

What is claimed is:

1. A mixer for the mixing of components, comprising:

a) a flexible mixing pouch which is configured and arranged to hold a first component prior to mixing, said flexible mixing pouch having a continuous inner surface that is non-retaining to said components, wherein a first portion of said surface opposably contacts a second portion of said surface during mixing, and wherein said components contact said inner surface during mixing; and b) a means for supplying a second component to the flexible mixing pouch, said means being attached to said flexible mixing pouch.

2. The mixer of claim 1 wherein said means for supplying said second component comprises a neck that has a first end and a second end, wherein said first end of said neck is attached to said pouch.

3. The mixer of claim 2 wherein said means for supplying said second component further comprises a cap configured to fit over said second end of said neck.

4. The mixer of claim 3 wherein said supplying means includes a protecting member and handling means.

5. The mixer of claim 2 wherein said neck is removably attached to said pouch.

6. The mixer of claim 2 wherein said supplying means comprises a valve attached to said neck.

7. The mixer of claim 6 wherein said valve is a manual valve or a check valve.

8. The mixer of claim 6 wherein said valve is a multiple-way valve.

9. The mixer of claim 2 wherein said supplying means comprises a frangible membrane attached to the inner surface of said neck.

10. The mixer of claim 9 further comprising a retaining structure attached to the inner surface of said neck, said retaining structure separating pieces of the broken frangible membrane from the components to be mixed.

11. The mixer of claim 2 further comprising a valve attached to said neck through which mixed components can be ejected.

12. The mixer of claim 11 wherein said valve is also a means for supplying a second component.

13. The mixer of claim 2 further comprising a needle or a tube attached to said neck through which mixed components can be ejected.

14. The mixer of claim 2 further comprising a single neck attached to said pouch, said neck being configured for introducing a second component into said mixing pouch and for expelling mixed components from said pouch.

15. The mixer of claim 1 wherein said first component is contained within said pouch and is a medically useful substance, and said second component is a liquid.

16. The mixer of claim 15, wherein said first component includes a powder.

17. The mixer of claim 16, wherein the first component is a bioceramic precursor powder.

18. A kit comprising:
 a) the mixer of claim 15 wherein said first component is in sterile form; and
 b) a syringe containing said second component in sterile form.

19. A method for preparing a medically useful composition, said method comprising the steps of:
 a) providing the mixer of claim 15 wherein said first and second components are in sterile form;
 b) introducing said liquid through the supplying means;
 c) mixing the combined components in said pouch; and
 d) removing the components from the pouch.

20. The mixer of claim 1 wherein said pouch is formed of an elastic material.

21. The mixer of claim 1, wherein said supplying means comprises a needle port or needle penetrable material.

22. The mixer of claim 1 wherein said supplying means comprises a permeable membrane.

23. The mixer of claim 1 wherein the mixer is adapted to be used with a mechanical mixing device that is adapted to accept said flexible pouch and to mix the components therein.

* * * * *